United States Patent
West et al.

(10) Patent No.: US 8,021,529 B2
(45) Date of Patent: Sep. 20, 2011

(54) ION MEASUREMENT/CALIBRATION CELL

(75) Inventors: Steven J. West, Hull, MA (US); Armin Kusig, Wayland, MA (US); Stephen Olsted, Rowley, MA (US); Jonathan Lowe, Scotland (GB); Xiaowen Wen, Lexington, MA (US)

(73) Assignee: Thermo Orion, Inc., Beverly, MA (US)

( * ) Notice: Subject to any disclaimer, the term of this patent is extended or adjusted under 35 U.S.C. 154(b) by 1370 days.

(21) Appl. No.: 11/185,545

(22) Filed: Jul. 20, 2005

(65) Prior Publication Data

US 2006/0237312 A1     Oct. 26, 2006

Related U.S. Application Data

(60) Provisional application No. 60/675,883, filed on Apr. 20, 2005.

(51) Int. Cl.
*G01N 27/27*     (2006.01)

(52) U.S. Cl. ........ 204/409; 204/400; 204/407; 324/438; 324/450

(58) Field of Classification Search .......... 204/401, 204/435, 409, 406–407, 400; 422/101–104; 324/438–450

See application file for complete search history.

(56) References Cited

U.S. PATENT DOCUMENTS

| | | | |
|---|---|---|---|
| 2,379,396 A | 7/1943 | Ziliotto | |
| 2,499,852 A * | 3/1950 | Dietz | 204/420 |
| 3,046,063 A | 9/1960 | La Bour | |
| 3,941,665 A | 3/1976 | Eckfeldt et al. | |
| 4,250,911 A | 2/1981 | Kratz | |
| 4,342,964 A | 8/1982 | Diamond et al. | |
| 4,600,494 A | 7/1986 | Bromberg et al. | |
| 5,002,657 A * | 3/1991 | Botts | 210/115 |
| 5,108,889 A | 4/1992 | Smith | |
| 6,317,129 B2 * | 11/2001 | Tomita | 345/467 |
| 6,684,880 B2 * | 2/2004 | Trueba | 128/200.16 |
| 7,041,206 B2 * | 5/2006 | Gephart et al. | 204/406 |

FOREIGN PATENT DOCUMENTS

| | | |
|---|---|---|
| DE | 1934793 | 1/1970 |
| EP | 0134622 | 3/1985 |
| EP | 0651246 A2 | 1/1988 |
| JP | 59065756 | 4/1984 |
| JP | 09006294 | 1/1997 |
| WO | WO99/39206 | 8/1999 |

* cited by examiner

*Primary Examiner* — Keith Hendricks
*Assistant Examiner* — Bach Dinh
(74) *Attorney, Agent, or Firm* — Cesari and McKenna, LLP; Martin J. O'Donnell

(57) ABSTRACT

A measurement/calibration cell for potentiometrically measuring ion concentration in a fluid interposes a barrier between measuring and reference electrodes and positions the measuring electrode at a sufficiently higher gravimetric potential above the reference electrode that seepage of electrolyte from the latter to the former is effectively precluded. A controller associated with the cell displays instructions and other desired information on a scrolling display such that a substantial amount of information can be presented in a relatively small display window.

9 Claims, 4 Drawing Sheets

ION MEASUREMENT/CALIBRATION CELL

The following application claims the priority of Provisional Application Ser. No. U60/675,883, "Improved Ion Measurement/Calibration Cell", filed Apr. 20, 2005.

BACKGROUND OF THE INVENTION

1. Field of the Invention

The invention relates to ion analyzers and, more specifically, to a combined ion measurement/calibration cell.

2. Background Information

A variety of industrial and other fields commonly rely on the measurement of ions in solution for such applications such as controlling industrial processes, assessing water quality, and the like. A particularly useful ion measurement and calibration cell is described in U.S. Pat. No. 4,600,494, issued Jul. 15, 1986 to Edward Bromberg et al. The teachings of this patent are incorporated herein by reference.

The '494 patent describes an ion analyzer cell having two modes of operation, the first a measurement mode in which the concentration of an ion in solution is measured, and the second a calibration mode in which the ion concentration in a carefully prepared and controlled sample is measured in order to calibrate the cell. The measurements are performed with a pair of potentiometric electrodes mounted in the cell. A first electrode of the pair serves as a measuring electrode; a second electrode of the pair serves as a reference electrode. The electrodes are separated by a partial baffle which largely, but not completely, isolates them from each other.

The baffle allows limited fluid communication between the electrodes to thereby provide the required electrical continuity for potentiometric measurement, while largely isolating their immediate environments to minimize contamination of the measuring electrode by seepage from the reference electrode. Even with such a baffle, however, there is still some flow ("backflow") of electrolyte from the reference electrode to the measuring electrode. When very small ion concentrations are being measured, this backflow can interfere with the ion measurement and degrade its accuracy.

Ion measurements are frequently made in industrial environments by users with little experience in, or knowledge of, precise chemical processes. For such users, it is important to provide as much assistance as possible in the use of the measuring apparatus, without unduly complicating the system. Printed manuals are often quickly lost or rendered illegible by spills and other abuses. Electronic displays are frequently too expensive or too limited to provide the required assistance.

SUMMARY OF THE INVENTION

Accordingly, it is an object of the invention to provide an improved ion measurement/calibration cell.

Further, it is an object of the invention to provide an improved ion potentiometric measurement/calibration cell which effectively prevents backflow of reference electrolyte to the measuring electrode.

Yet another object of the invention is to provide an ion analyzer having a display that guides the user in the operation of the analyzer.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
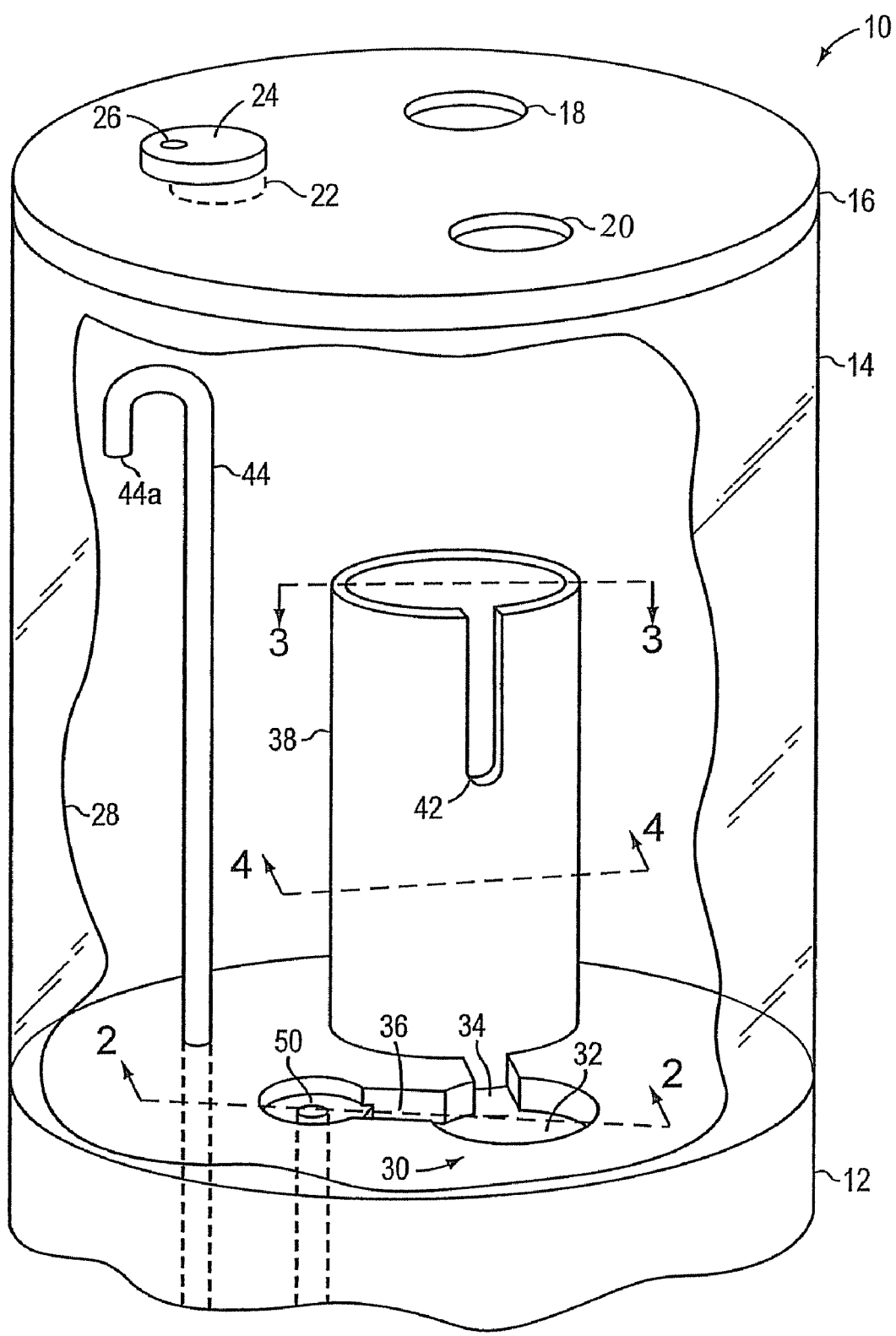
FIG. 1 is a view in perspective of an improved ion measurement/calibration cell in accordance with the present invention.
Figure 2:
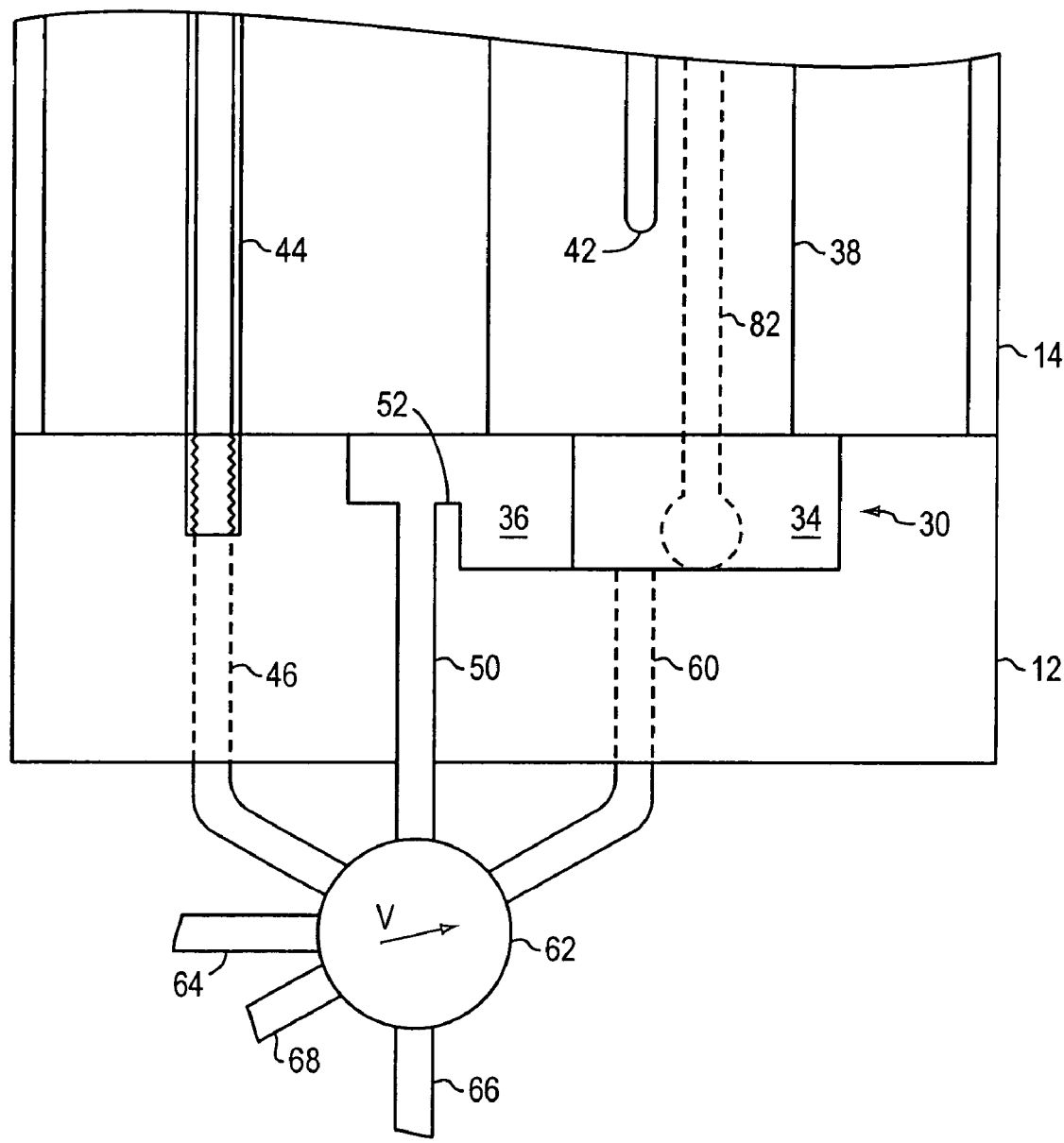
FIG. 2 is a partial cross-sectional view along the lines 2-2 of FIG. 1.

Referring now particularly to FIGS. 1 and 2, one embodiment of a measurement/calibration cell in accordance with the present invention has a base 12 into which is inset a generally cylindrical wall 14 to which is fitted a cover 16. Ports 18, 20 and 22 extend through the cover; port 22 is closed by a hatch 24 that is pivoted about a pin 26 extending through the hatch into the cover to enable access to the port.

Figure 4:
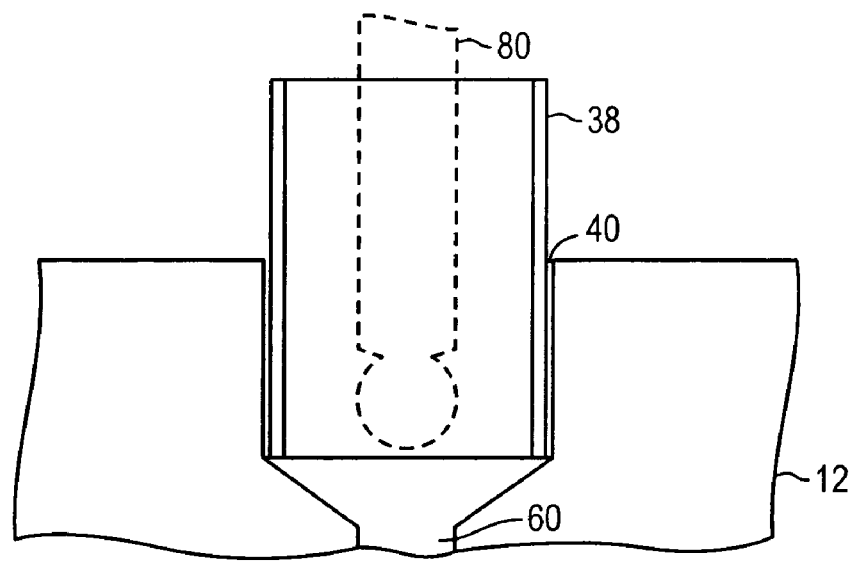
FIG. 4 is a partial cross-sectional view along the lines 4-4 of FIG. 1.

In FIG. 1, the interior of the cell 10 (as seen through breakaway 28) includes a trough or channel 30 having a generally cylindrical center portion 32 and side arms 34, 36 radiating therefrom; the channel is formed in the upper surface of base 12, advantageously by machining or the like. The channel 32 extends up to, but not into, a cylindrical shell 38 which is snugly fitted into a bore 40 (see FIG. 4) in the base 12 at its lower end to form a fluid-tight seal therewith. The shell 38 has a notch 42 extending downwardly from its upper edge. A siphon 44 having an inverted inlet 44a is threaded into the base 12. It connects to a drain 46 extending through the base.

Figure 3:
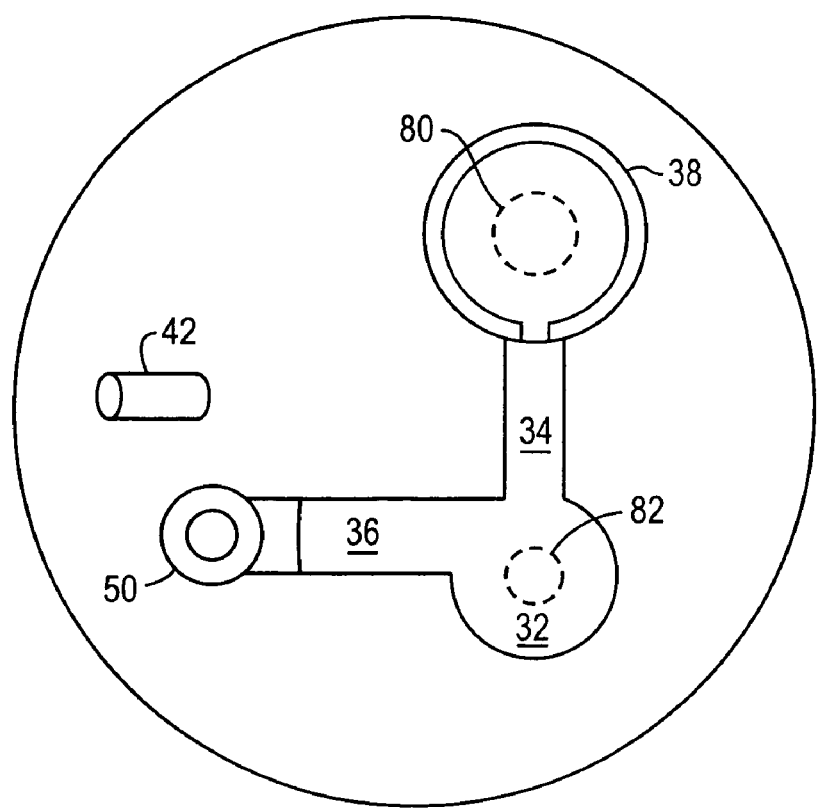
FIG. 3 is a top plan view of the interior of the cell of FIG. 1.

Referring now particularly to FIGS. 2 and 3, the channel arm 36 connects to a drain 50 formed in the base 12. A lip 52 (FIG. 2) partially terminates the extension of the channel arm 36, leaving the upper portion of the channel arm in fluid connection with the drain 50 and forming a weir for liquid flowing from the channel arm into the drain. The weir ensures retention of a certain minimum level of fluid in the channel 30.

A sample liquid whose ion concentration is to be measured is supplied to the cell 10 via a channel 60 (see FIG. 4) connecting to the interior of the shell 38. The sample fills the shell until its level rises to the lower edge of the notch 42, then spills over into the channel arm 34 from which it travels to channel segment 32 and thence along arm 36 to drain 50.

As shown in FIG. 2, a multi-position valve 62 is connected to the drains 46 and 50 and to the sample inlet channel 60. Sample liquid is supplied to the channel 60 through the valve 62 via an inlet line 64, and is drained from the cell through drain 50, valve 62, and an outlet line 66. An air line 68 is also connected to the valve 62 to facilitate mixing within the cell when the cell is operated in the calibration mode.

The cell 10 accommodates a pair of potentiometric electrodes. A first (or measuring) electrode 80 (shown in dotted outline in FIGS. 3 and 4) is inserted through port 18 (FIG. 1) which is vertically aligned with the interior of shell 38. A second (or reference) electrode 82 (shown in dotted outline in FIGS. 2 and 3) is inserted through port 20 (FIG. 1) which is vertically aligned with center section 32 of channel 30. The head of the electrode 82 extends into the center section, so that it is swept by fluid escaping the shell 38 via notch 42. The ports 18 and 20 are so sized with respect to the electrodes 82 and 80, respectively, as to present a snug fit when the electrodes are inserted through them into the cell. This helps provide a relatively airtight seal for the cell to assist siphoning action as described below.

As is the case with U.S. Pat. No. 4,600,494, described above, the cell 10 operates in two modes, namely, measurement mode and calibration mode.

In measurement mode, the valve 62 is operated to provide sample solution to the cell via inlet line 64, valve 62, and channel 60. In this mode, the sample flows upwardly through channel 60 into shell 38 until its level reaches notch 42, which is located sufficiently high on the shell 38 that at least an active portion of the electrode 80 (i.e., a portion that must be wetted by a liquid to perform a measurement) is immersed in the liquid flowing through the shell. At this point the sample spills over into the channel 30 from which it exits to drain 66 via channel 50 and valve 62. The channel 30 confines the flow and ensures a small but well-defined volume for measurement purposes. In spilling over the shell 38 through the notch 42, a continuous liquid film, and thus conductive path, is maintained in the channel 30 in which the reference electrode 82 is immersed such that at least an active portion of this electrode is exposed to the liquid flowing through the channel. It should be understood that a continuous film could also be maintained without the notch 42, although a higher flow rate of liquid would be required since overflow from the shell would no longer be confined to one location on the shell 38. Thus the notch is advantageous but not absolutely necessary.

The cell is advantageously operated in a continuous measurement mode in which liquid sample continuously follows the path described and its ion concentration is either continuously or repeatedly measured as it does so. Of course, it may also be operated on an intermittent basis. As the sample sweeps along its path, it passes over the head of measuring electrode 80 (FIGS. 3 and 4) and thence over the head of reference electrode 82 (FIGS. 2 and 3), thus providing electrical continuity between the electrodes and enabling measurement of the electrical potential between them. The potential is a function of the ion concentration of the liquid washing over them. The shell 38, as it fills to the level of notch 42, creates a gravitational potential that drives the flow outwardly from the shell in the downstream direction, i.e., from measuring electrode 80 toward reference electrode 82. Thus, seepage of electrolyte from reference electrode 82 back to measuring electrode 80 is effectively precluded and the ability to measure smaller ion concentrations than would otherwise be practical is significantly enhanced because a source of low-level interference is thereby eliminated. This is particularly important when measuring Na ion concentration in samples, since such measurements are especially susceptible to interference from seepage of electrolyte from the reference electrodes commonly used in such measurements. The present invention thus enhances the accuracy of such measurements.

In the calibration mode, valve 62 is positioned to admit both sample (from line 64) and air (from line 68) into the cell via line 60, and to establish communication between drains 46 and 66. In this mode, valve 62 operates to close drain 50, and the level of sample in the cell is allowed to rise until it reaches the uppermost point of siphon 44. At this time the siphon commences to operate and begins to drain sample liquid via drain 46 and thence through valve 62 into drain 66 from which it may suitably be disposed of. The drainage continues until the liquid level drops to the level of the inlet aperture 44a of siphon 44.

After the drainage starts, a second valve (not shown) can be used to shut off the supply of sample liquid. When the drainage ceases, the cell contains a well-defined volume of sample. A potentiometric measurement of the ion concentration of the sample is then taken to establish a first reference point for calibration of the cell. Next, hatch 24 is opened, and preferably successive aliquots of precisely defined, concentrated solutions of the ion whose concentration is to be measured by the cell are added to the sample, the aliquots being of different concentrations, and successive potentiometric measurements are made to thereby establish second and third reference points for the sample. From these the desired calibration may be obtained.

Air is bubbled through the sample during calibration to insure good mixing of the aliquots and the sample; the valve 62 may also be operated to provide continuous recirculation of the captured sample through conduits 46 and 60 and valve 62 by means of the injected air, to thereby further insure thorough mixing of the sample and the added reagent. When the measurements are completed, the valve 62 is operated to allow the sample to drain through either or both or drains 46 and 50, valve 62, and drain 66. Preferably, the valve is further operated to allow sample to run through the cell for a brief time to thoroughly flush the cell prior to making actual measurements of sample concentration.

It will be understood that the valve 62 may be operated manually or by a simple programmed or programmable controller as are commonly used in industry. Further, the valve may be implemented as a set of several valves, each of which performs one or more of the multiple switching functions described for the single valve 62 shown herein.

Figure 5:
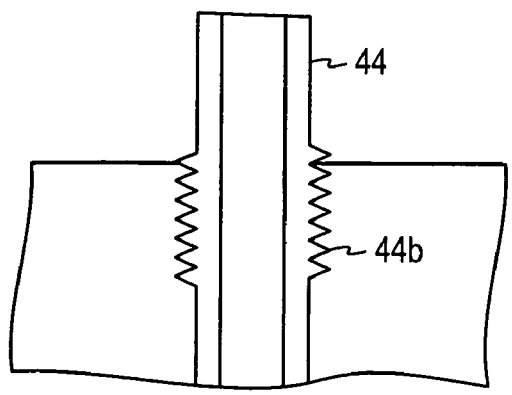
FIG. 5 is a partial sectional view of a preferred form of siphon construction.

As noted earlier, the siphon 44 is preferably adjustably connected to the base 12 so that the height of its inlet above the base may be changed to thereby allow precise adjustment of the sample volume of the cell in calibration mode. This is readily accomplished by providing the siphon with a threaded lower end which mates with a correspondingly threaded bore in the base 12, as shown at 44b in FIG. 5. The height of the siphon inlet, and thus the sample volume, may then be adjusted simply by rotating the siphon with respect to the base. Once a desired volume has been achieved, it may thereafter be maintained by securing the siphon against further movement, e.g., by application of epoxy or other suitable locking means.

The accuracy of the calibration is further enhanced by ensuring an air-tight seal between the wall 14 and cover 16, as well as at the ports 18 and 2, when electrodes are inserted through them, and at the port 22 This ensures that, during calibration, the siphoning action begins at the same level for each calibration. The introduction of air bubbles into the cell during calibration will then increase the internal air pressure within the cell and help the siphon to commence operation at a reproducible sample level.

Figure 6:
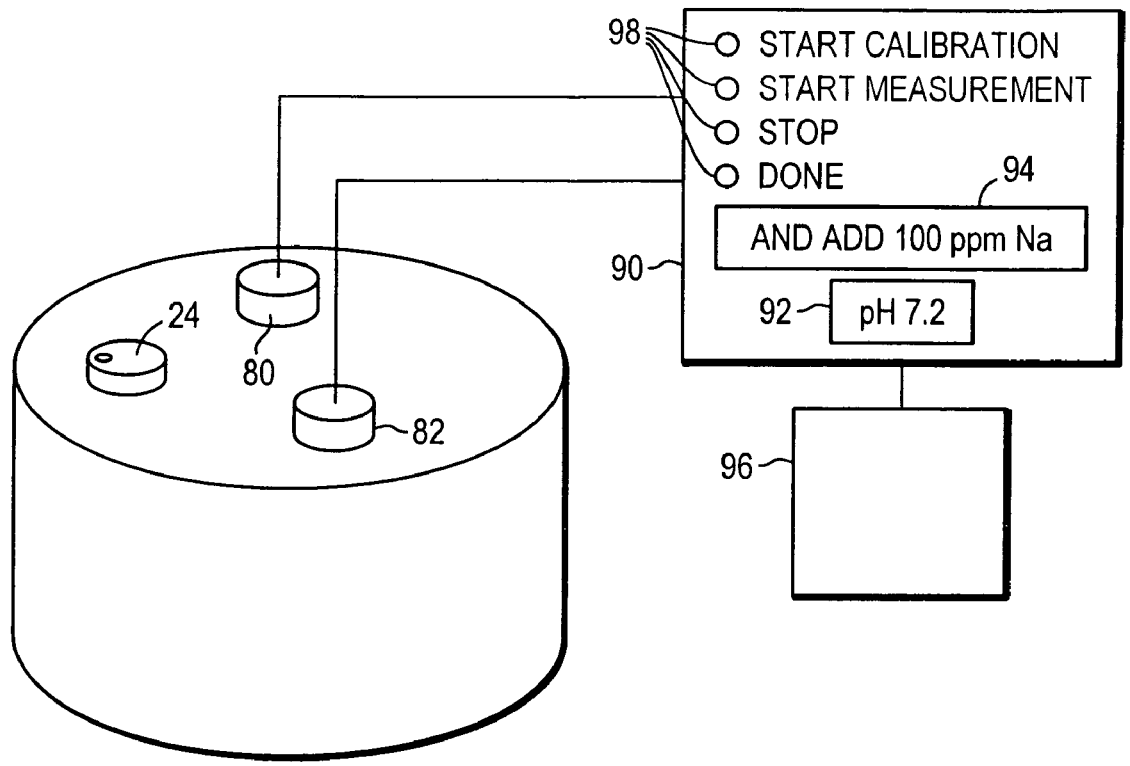
FIG. 6 is a pictorial view of the measurement/calibration cell system of FIG. 1 shown connected to a preferred form of display screen of the present invention.

Turning now to FIG. 6, the electrodes 80, 82 of cell 10 are connected to a control and display panel 90. The panel 90 displays the measured ion concentration at 92, preferably, though not necessarily, in the form of an LCD display which are now quite economical. Importantly, it also displays instructions for use of the cell in a scrolling display 94. The panel is driven from a processor 96 which performs the calculations required for calibration and measurement, and which also stores, and controls the display of, information for the user. Programmable processor chips for this purpose are now commonly and inexpensively available, and the processor is thus preferably incorporated into the display module. It will be understood that alternative ways of driving the control and display panel may also be used. For example, a general purpose computer such as a general purpose computer may be used, but at increased expense. Pushbuttons 98 may be provided to control operation of the panel. For example, there may be provided a "Start calibration" button; a "Start measurement" button; a "Done" button; and a "Stop" button. Other or alternative buttons may, of course, be provided.

In accordance with the present invention, the display 94 displays text in a scrolling manner. Preferably, the display instructs the user as to operation of the cell at each step, so that even an inexperienced user can quickly be brought up to speed as to proper operation of the cell in all its aspects. The words of the instruction move across the display, e.g., from right to left, preferably in a continuous manner, although not restricted to this mode. Thus, although the physical width of the display is limited, it can display a message of length greater than the display width.

For example, during calibration it might be necessary to add a certain amount of reagent to the sample volume. An appropriate instruction might be as follows:

"To establish the first calibration point, uncover the reagent port and add 100 ppm Na to the sample in the cell. Close the cover and allow the reagent to thoroughly mix with the sample for 90 seconds."

While this instruction could be displayed on the screen in its entirety at any time, to do so consumes considerable area. Thus, the typeface of the displayed instruction must be made small or the display area large. The former approach is psychologically uninviting, particularly when the cell is to be used in an industrial environment where accessibility is limited or lighting is poor. The latter approach leads to unacceptably large, and expensive, displays.

In accordance with the present invention, the display 94 is of limited length and height and of limited area. Preferably, its height is little more than that of type of, e.g., 20 point height, and its length, e.g., 50 characters. It will be understood that other sizes and lengths may be used. To accommodate the entire instruction, the instruction is scrolled across the screen. Preferably, this is done repeatedly, until the operator indicates that the indicated operation has been performed, e.g., by pressing the "Done" button 96b. The benefits of a scrolling display are several. First, inexpensive, custom-LCD displays have a limited number of segments that can be switched on or off. Most off-the-shelf displays can accommodate, for example, only 160 segments. Scrolling thus enables a high information content with a small number of segments. Further, not only does this display conserve space, it appears to provide a psychological benefit as well, i.e., it appears that the user quickly absorbs the directed instructions and becomes proficient in use of the cell more readily than might otherwise be expected.

From the foregoing it will be seen that we have provided an improved measurement/calibration cell. The cell is simple and economical to construct, yet significantly improves the accuracy of ion measurements, an advantage that is especially important when measuring the concentration of ions such as Na ions which are particularly susceptible to interference from commonly-used reference electrolyte. The configuration of the cell of the present invention ensures that the flow is essentially one-way, from the measuring electrode to the reference electrode; backflow from the reference electrode to the measuring electrode is thus effectively prevented.

Further, we have provided a display that enables even an inexperienced user to perform measurement and calibration operations with confidence because step-by-step instructions can be displayed visually and in a manner (scrolling display) that appears to be especially amenable to assimilation by the user. Preferably, the text of the instructions scrolls across the display from one side to the other, such that only a fragment of an instruction is displayed at any one time. A single line of display has been found to be suitable, although other formats (e.g., multiple lines, vertical scrolling, etc.), may also be used. The display is readily implemented by commercially available LCD displays, although, of course, other displays such as LED displays, among others, may be used. The size of the display can be spatially limited yet, because of its nature, it can present a substantial amount of information in characters of a size as to be readily discernable even under the kind of adverse conditions (e.g., poor lighting, cramped space, among others) not infrequently encountered in industrial installations.

What is claimed is:

1. A measurement/calibration cell for measuring the ion concentration of liquids as the liquids flow through the cell, comprising:
    A. An enclosure for receiving a first electrode therein and connected to a first channel for delivering liquid to the interior of said enclosure, said enclosure sized to accommodate a first volume of sample at least sufficient to immerse an active portion of said electrode during a measurement and to overflow at a first level after receiving some volume greater than said first volume,
    B. A second channel positioned below said first level to receive sample overflowing from said enclosure so that when operated in measurement mode in which liquid flows through the cell and ion concentration is measured, the surface level of liquid in said second channel will be at a second level below said first level to cause sample to flow from said enclosure to said second channel and not in the reverse direction due to gravimetric potential differences between said surface levels, said second channel sized to accommodate a second electrode therein such that an active portion of said electrode is immersed during a measurement, and
    a siphon mounted in a chamber for defining a specified volume for calibrating said cell, and in which said siphon is mounted such that its height above a base level is adjustable to thereby adjust the calibration volume.

2. A measurement/calibration cell according to claim 1 in which said enclosure comprises a shell for receiving a first electrode therein and having an aperture formed therein for the discharge of liquid therethrough.

3. A measurement/calibration cell according to claim 1 which includes a base, said second channel being formed in said base to receive liquid from said enclosure.

4. A measurement/calibration cell according to claim 2 in which said second channel comprises a groove having a center portion for receiving said second electrode and including a first channel arm leading from said shell to said center portion.

5. A measurement/calibration cell according to claim 4 in which said second channel includes a second channel arm leading from said center portion to a drain.

6. A measurement/calibration cell according to claim 1 in which said siphon comprises a tube having an inlet at one end thereof and a threaded surface at the other end thereof for threadedly engaging said base to thereby enable adjustment of the height of the inlet above said base by rotating the threaded end with respect to said base.

7. A measurement/calibration cell according to claim 1 which includes a display for providing instructions to a user and in which the instructions are displayed in the form of words which move across the display in a continuous manner without user intervention.

8. A measurement/calibration cell according to claim 7 in which said words move across said display in a single line.

9. A measurement/calibration cell according to claim 7 in which said display comprises an LCD display.

* * * * *